United States Patent [19]
Kobayashi et al.

[11] Patent Number: 5,508,760
[45] Date of Patent: Apr. 16, 1996

[54] OPHTHALMIC EXAMINATION APPARATUS FOR SCANNING, IMAGING AND OBSERVING THE EYE

[75] Inventors: Koji Kobayashi; Hiroki Matsui, both of Chofu, Japan

[73] Assignee: Kowa Company Ltd., Japan

[21] Appl. No.: 200,821

[22] Filed: Feb. 23, 1994

[30] Foreign Application Priority Data

Feb. 25, 1993 [JP] Japan .................................. 5-035943

[51] Int. Cl.$^6$ ..................................................... A61B 3/10
[52] U.S. Cl. ......................... 351/221; 351/205; 351/216
[58] Field of Search .................................. 351/200, 205, 351/221, 237, 243, 216; 385/31

[56] References Cited

U.S. PATENT DOCUMENTS

| | | | |
|---|---|---|---|
| 4,786,161 | 11/1988 | Müller et al. | 351/205 |
| 5,071,246 | 12/1991 | Blaha et al. | 351/221 |
| 5,210,808 | 5/1993 | Grasso et al. | 385/31 |

Primary Examiner—William L. Sikes
Assistant Examiner—Huy Mai
Attorney, Agent, or Firm—Adams & Wilks

[57] ABSTRACT

An ophthalmic examination apparatus for scanning, imaging and observing the fundus of the eye comprises an optical system including a first laser source and a laser scanner, a base unit containing a synchronizing circuit for the laser scanner and a video monitor, an image processing unit, and a second laser light source unit detachably connectable to the optical system unit and optically connected with the scanning optical system through an optical fiber. An optional auxiliary optical system unit is provided for attachment to the optical system to observe the anterior chamber as well as the fundus of the eye. An optical device is incorporated to control the direction of light propagation generated by the second laser light source unit. The ophthalmic examination apparatus facilitates a diverse range of user needs, simplifies maintenance and transport and permits the configuration of an economical ophthalmological device to be configured.

17 Claims, 6 Drawing Sheets

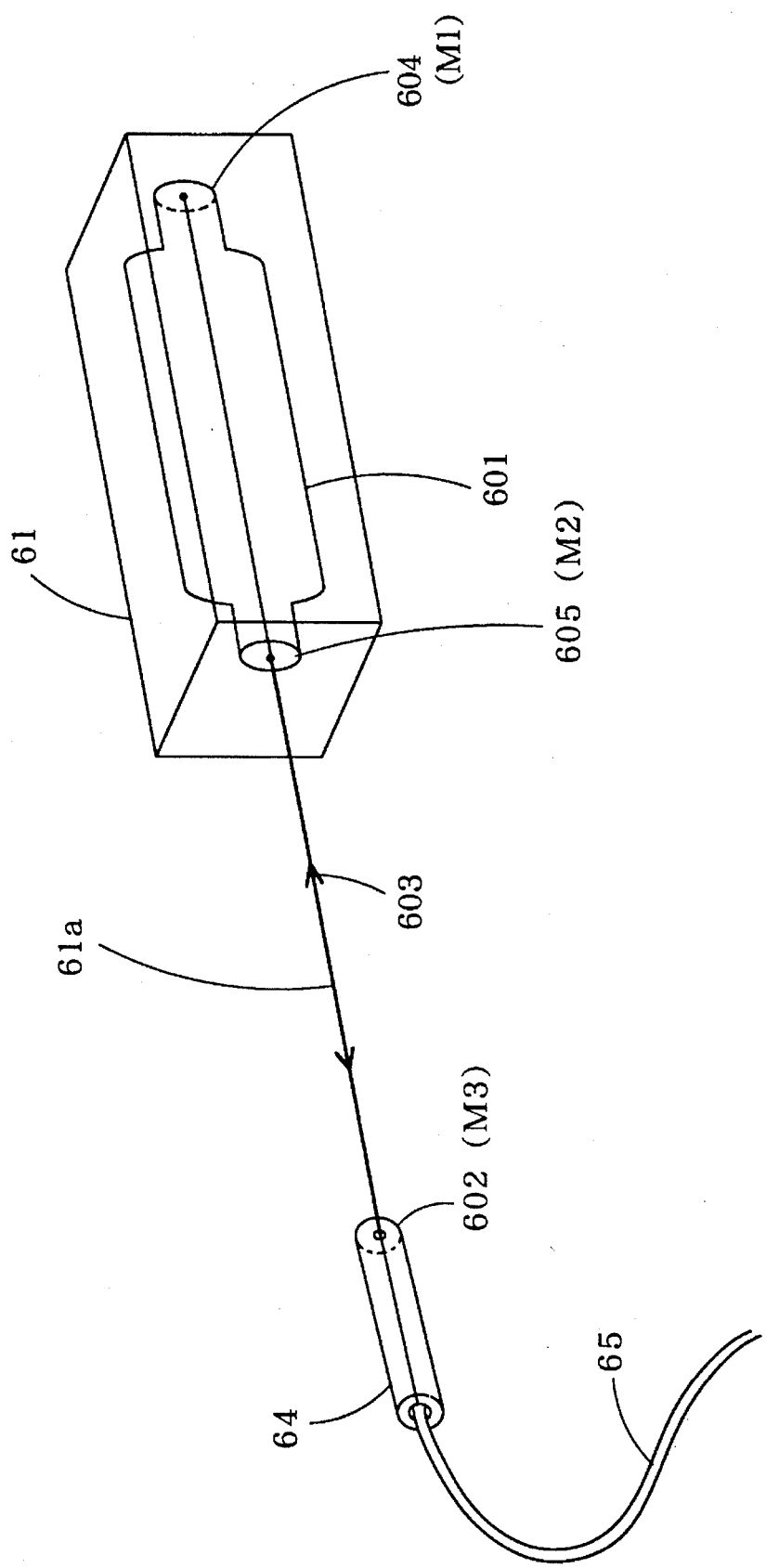

OPHTHALMIC EXAMINATION APPARATUS FOR SCANNING, IMAGING AND OBSERVING THE EYE

FIELD OF THE INVENTION

The present invention relates to an ophthalmic examination apparatus, and more particularly to an ophthalmic examination apparatus whereby the fundus of an eye is scanned two-dimensionally by a laser beam from a laser light source, and light reflecting from the eye is detected by a light receiving element and photoelectrically converted to obtain image information of a prescribed part of the eye.

BACKGROUND OF THE INVENTION

Recent years have seen the development of electronic ophthalmological devices that utilize laser scanning. Such instruments are called scanning laser ophthalmoscopes (which herein shall be abbreviated as "SLO"), and particular progress has been made with such devices for use in observing the eye fundus (described, for example, in JP-A-62-117524, USP 4764005; and JP-A-64-58237, U.S. Pat. No. 4854692).

With a conventional SLO, by scanning the eye fundus two-dimensionally by a laser beam passing through the center of the pupil, and receiving, photodectrically converting and amplifying the light reflected by the eye fundus from a larger area around the pupil, it is possible to display a real-time video image of the eye fundus on a TV monitor with a low brightness and a high S/N ratio. Also, the effect of non-essential scattered light can be screened out by using an optical system with a confocal arrangement system, thereby producing a marked improvement in fundus image resolution and contrast.

Among other advantages provided by these new instruments that are producing major innovations in ophthalmology are that they make it possible to decrease greatly the amount of fluorescent agent that needs to be administered for fluorescent angiography of the eye fundus, and by modulating the scanning laser beam it becomes possible to examine visual function while observing the eye fundus, and the monochromatic properties of lasers make it possible to carry out precision examination of the fundus, and real-time three-dimensional observation (cf. JP-A-1-113605, U.S. Pat. No. 4,900,144, Optics Communications, vol. 87, 1992, pp 9–14).

To obtain the large amounts of information required for diagnoses using such ophthalmic examination apparatuses, it is desirable to prepare a plurality of laser light sources of different wavelengths. For example, infrared, red, yellow, green, blue and other wavelengths are used for different image observation applications, as well as, in the case of angiography, fluorescein angiography (FAG) and indocyanine green angiography (ICG) and the like.

To meet the advanced needs of ophthalmologists, this means that it is necessary to prepare three or four laser light sources and to incorporate all of them in the optical system of the apparatus. This results in an increase in the size of the optical system (optical head): an example of one such apparatus is illustrated on page 444 of "Noninvasive Diagnostic Techniques in Ophthalmology," (Springer, Berlin, 1990).

During use of the foregoing conventional of ophthalmological apparatus, the patient is seated on a chair, facing the optical head, which is moved vertically and horizontally to bring it into alignment with the optical axis of the eyeball. In a clinical setting, a large optical head is undesirable because it makes the machine more difficult for the ophthalmologist to operate and also causes the patient unnecessary anxiety.

In view of the large size of laser light sources and the heat they generate, especially short-wavelength, visible-light gas lasers, it is generally preferable for the laser tube to be located away from the optical head, which has led to the use of a flexible optical fiber to link the laser light source and optical system, as described by JP-A-60-132536, JP-A-1-101959, and JP-A-3-63303, for example. JP-A-3-63303 even describes the use of an optical fiber connection between the confocal aperture of the optical system and the light receiving element, with the aim of decreasing the size of the optical head.

The diversification of application needs and structural complexity are problems associated with conventional ophthalmic examination apparatuses (SLO). The laser source used by an ophthalmologist conducting an examination of the eye fundus will vary depending on the ailment involved. Thus, one source might be used to check for diabetic degeneration, another to examine ophthalmic circulation, for example. That is, use of the most diagnostically effective wavelength will differ from ailment to ailment. Even when only single wavelength capability is initially specified, advances in clinical research often make it necessary at a later date to expand the laser source capabilities or upgrade a system's image processing performance, and manufacturers have to be able to respond to such individual user requirements.

Conventional ophthalmic examination apparatuses equipped with a single wavelength laser cannot meet such diversifying needs. On the other hand, initially configuring the apparatuses with a multiplicity of lasers, including image processing functions, increases the size and the cost and makes them more difficult to maintain and expensive to transport, There, such apparatuses are unable to answer the needs of high-level medical treatment, in terms of both economics and efficiency.

Another drawback with conventional ophthalmic examination apparatuses, especially those which use an optical fiber connection between the laser light source and the optical system, is the of degradation of picture quality. As the aim is to obtain an image of the eye fundus or other such part of interest by two-dimensional scanning with a laser beam, in order to improve the resolution it is necessary to reduce the size of the scanning light spot. As such, it is advisable to use a single-mode optical fiber having a core diameter no larger than 10μm.

However, when the beam from the laser tube is tightly focused onto the end face of the optical fiber to effect the link, light reflected from the end face of the fiber propagating back to the laser tube can destabilize the lasing action and cause the power output to fluctuate.

How this happens, in the case of a gas laser using a round tube, is illustrated by FIG. 6. A laser beam 61a emitted from a laser tube 601 in the laser light source 61 is linked to an optical fiber 65 by a connector 64.

To increase the transmission efficiency of an optical fiber, especially a single-mode fiber, the laser beam has to be focussed precisely onto the center of the core.

However, with the beam aligned precisely with the core center for maximum transmission efficiency, a return component 603 from a slight reflection from the fiber end face 602 travels back along the path of beam propagation and into the laser tube 601. It is as if a composite resonator has been formed between resonator mirrors (M1) 604 and (M2) 605 and the fiber end face 602, and can produce extreme instability of the lasing action and a major degree of fluctuation noise.

Another problem encountered when an optical fiber is used to transmit the laser beam is that movement or vibration of the fiber can cause beam power variation. Although conventional ophthalmic devices such as laser coagulators and the like use an optical fiber to transmit the laser beam, such power variation is not a significant problem, either because a large-core multimode fiber is used or because slight variations in beam power are not a hindrance to the objective of fixating the fundus.

However, with SLOs and other such imaging systems which are required to provide images with a high S/N ratio, the variations in beam power resulting from the conventional use of optical fibers gives rise to noise which is superimposed on the TV pictures, degrading the picture quality, which is a problem particularly when viewing images on a real-time basis.

The object of the present invention is to provide an ophthalmic examination apparatus that can answer the diverse needs of clinical ophthalmology without increasing its size and cost and is easy to maintain and transport, and which provides good images of the region being examined, with no degradation in picture quality even when the laser light source and optical system are linked by an optical fiber.

SUMMARY OF THE INVENTION

In accordance with the present invention, the above object is achieved by an ophthalmic examination apparatus comprised of separate optical system, base, image processing and laser light source units, and optionally further comprises an auxiliary optical system unit that can be detachably attached to the optical system unit for observing the anterior chamber and other regions as well as the eye fundus, and when an optical fiber is used to transmit the laser beam between the units, may be additionally configured to reduce the effect of beam power variation noise produced by light returning from a fiber end face or from other causes.

The above configuration in which each part of the apparatus is a separate unit makes it possible to reduce the size of the apparatus on a unit by unit basis. Also, as a user can start by purchasing just the optical system unit and base unit, then if necessary expand the system at a later date by adding an image processing unit or laser light source unit, there are major cost advantages, and for a manufacturer, maintenance and transport are facilitated.

Furthermore, the optional auxiliary optical system unit that can be attached to the main optical system unit makes it possible to expand the range of observation regions to include the anterior chamber.

Moreover, even when an optical fiber is used to transmit the laser beam, the effect of beam power variation noise on the TV picture is suppressed, making it possible to observe images with a good S/N ratio.

BRIEF DESCRIPTION OF THE DRAWINGS

FIG. 6 illustrates reverse propagation of the laser beam.

DETAILED DESCRIPTION OF THE PREFERRED EMBODIMENTS

Details of the embodiments of the invention will now be described, with reference to FIGS. 1 to 5.

Figure 1:
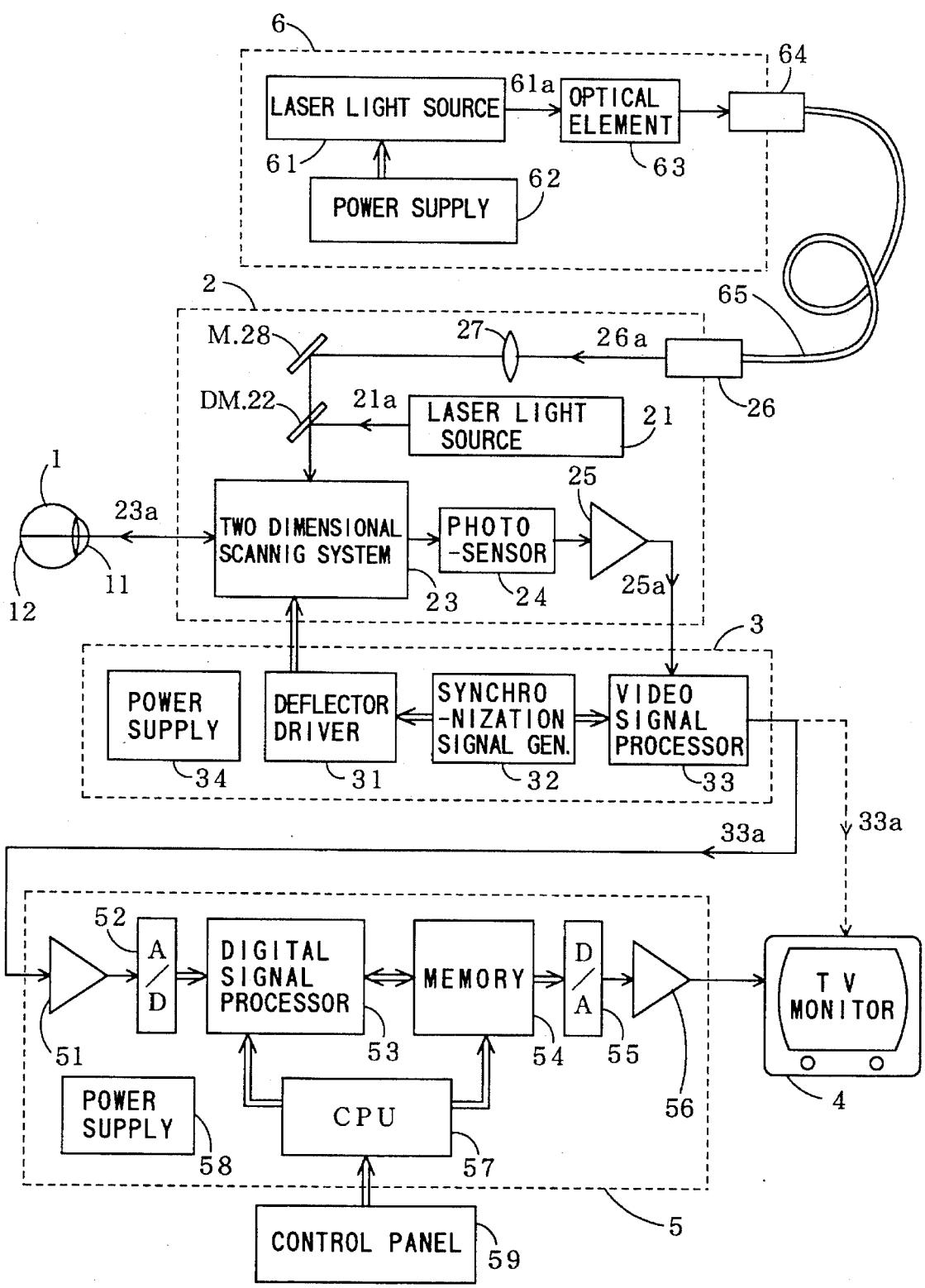
FIG. 1 is a block schematic diagram showing the arrangement of an ophthalmic examination apparatus according to this invention.

FIG. 1 shows the overall system configuration of an ophthalmic examination apparatus according to this invention. In FIG. 1, reference numeral i denotes an eye being examined. An optical system unit 2 is arranged facing the eye 1.

The optical system unit 2 incorporates a first laser light source 21 that produces a prescribed laser beam. The laser light source 21 is a semiconductor laser or a He-Ne laser or other such small laser device. A laser beam 21*a* emitted by the laser light source 21 is reflected by a dichroic mirror 22 into a two-dimensional optical scanning system 23.

The scanning system 23 scans the laser beam two-dimensionally, producing a raster 23*a* corresponding to a standard TV scanning raster. This raster laser beam is projected onto the eye fundus 12 via the pupil 11. Light reflected from the eye fundus 12 passes back through the two-dimensional scanning system 23 to a photosensor 24, which converts the intensity of the reflected light to an electrical signal, which is amplified by an amplifier 25 and output from the optical system unit 2.

The scanning system 23 is provided with a galvanometer mirror, an acoustooptical deflector, a polygonal mirror, an oscillating mirror or other such deflection device for deflecting the laser beam to effect scanning in two dimensions. This laser beam deflection is controlled by a deflector drive circuit 31 in a base unit 3.

The deflector drive circuit 31 has the corresponding control drivers for the deflector being used, and a sweep sawtooth waveform generator, and operates in accordance with synchronizing signals from a synchronization signal generator 32. A detection signal 25*a* output from the optical system unit 2 is subjected to primary processing such as clamping, gamma correction and synchronization adding by a video signal processor 33, and is then output from the base unit 3 as video output signal 33*a*. The base unit 3 has a power supply circuit 34 which supplies power to all the electrical systems of the optical system unit 2 and base unit 3.

All that needs to be done to be able to view images of the eye fundus on a monitor is to add a TV monitor 4 to the optical system unit 2 and base unit 3. This gives a basic system that is well equipped for precise clinical observation of the state of the eye fundus on a real-time basis.

For ophthalmological research applications involving image processing, the apparatus can also be configured with an image processing unit 5. The video signal 33*a* from the base unit 3 is amplified by an amplifier 51 in the image processing unit 5, and is then converted by an A/D converter 52 to 8-bit digital data, for example.

In a signal processing circuit 53, this digital data is subjected to secondary processing such as spatial filtering, gray-scale conversion and addition averaging, and is then stored in a storage unit 54.

To ensure sufficient storage for the large quantities of image data, the storage unit 54 can be equipped with a multiplicity of storage means that includes magnetic and optical disks as well as semiconductor video RAM.

Digital image data output from the storage unit 54 is subjected to D/A conversion by a D/A converter 55, amplified by an amplifier 56 and output to be displayed on a TV monitor 4. The signal processing circuit 53 and storage unit 54 and the like are controlled by a central processing unit (CPU) 57.

The CPU 57 contains a microprocessor, memory elements and various interface devices. Software stored in memory can be used to carry out image enhancement, three-dimensional measurement and other processing in accordance with commands issued from a control panel 59 provided with a keyboard and a pointing device such as a trackball or mouse. Provided in the image processing unit 5 is a power supply circuit 58 that provides power to the internal circuitry of the image processing unit 5.

An effective way of obtaining precision diagnoses is to observe the fundus using laser light sources of various wavelengths. For this, the apparatus of this invention can be equipped with a laser light source unit 6 containing a second laser light source 61 that generates a laser beam with a different wavelength from that of the laser light source 21 in optical system unit 2.

The relatively small size and low heat generation of an infrared or visible light wavelength semiconductor or He-Ne laser enables such a laser to be housed within the optical system unit 2 without any problem. However, an Ar$^+$or other such laser has a large tube and generates considerable heat and, therefore, has to be forcibly cooled by means of a fan or the like, which makes it difficult to house such a laser source in the optical system unit positioned in close opposition to the eye being examined.

This invention therefore provides a separate, laser light source unit 6, that has a laser light source 61 and a laser power supply 62 for an Ar$^+$or other such laser. A laser beam 61a emitted by the laser light source 61 passes via an optical element 63 and the connector 64 to the end face of the optical fiber 65. As described below, the optical element 63 contains an element that controls the direction of optical propagation, a filter and lens.

The optical fiber 65 can be connected to, and disconnected from, the optical system unit 2 by means of a connector 26. The laser beam 26a from the second laser light source is collimated by lens 27, reflected by mirror (M) 28 and combined with the laser beam 21a from the first laser light source by the dichroic mirror 22.

By thus providing a laser light source of a different wavelength as a separate laser light source unit 6 that can be connected by an optical fiber to the optical system unit 2, the addition of additional laser light sources with other wavelengths can be added, making it possible to readily respond to changing needs.

Figure 2:
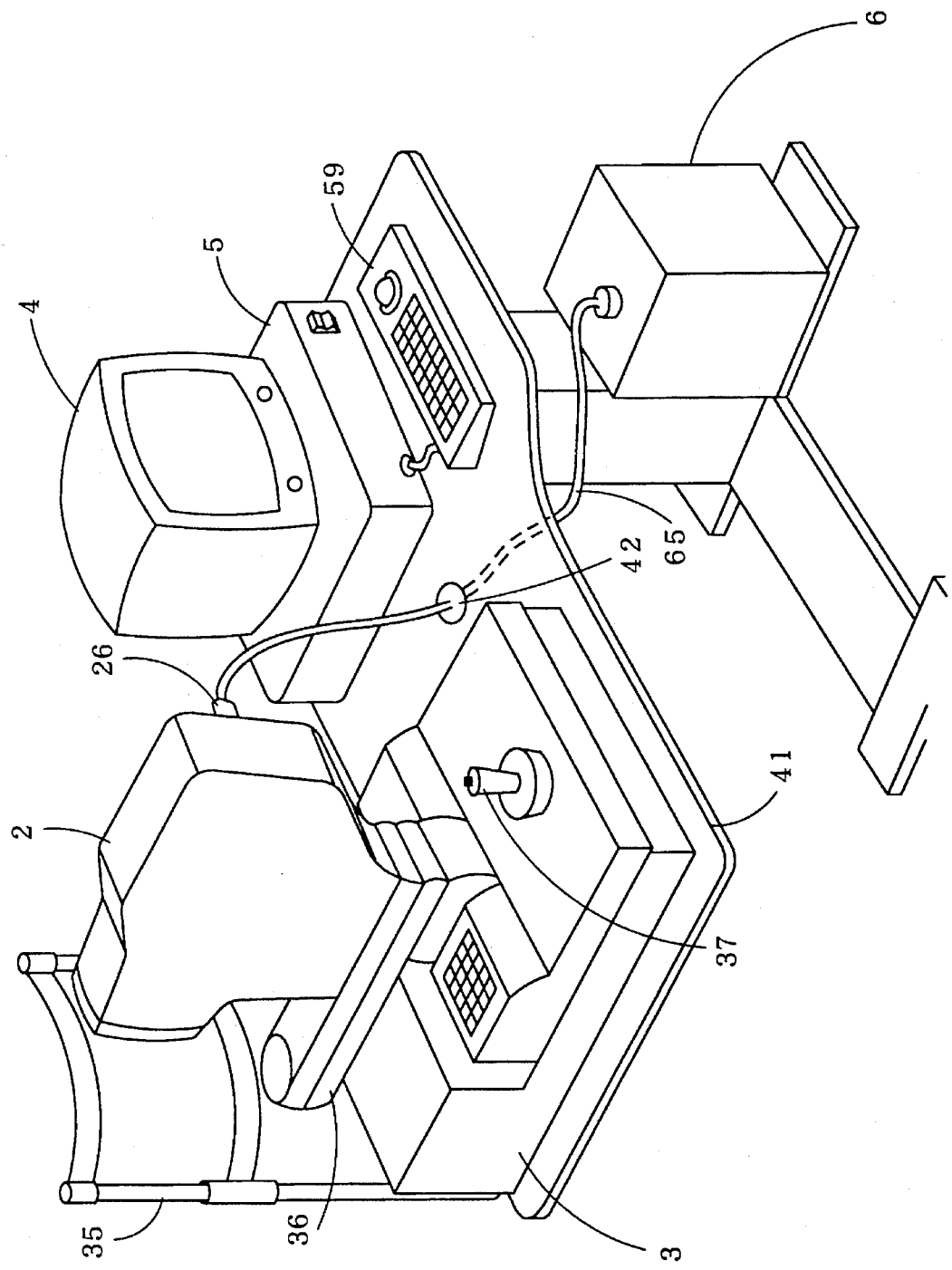
FIG. 2 is a perspective view of the overall system arrangement of the ophthalmic examination apparatus of the invention.

FIG. 2 shows the ophthalmic examination system apparatus of the invention. The base unit 3 and the optical system unit 2 comprising the basic system configuration are arranged on a table 41. The base unit 3 is provided with a chin-rest 35 for the patient. The optical system unit (optical head) 2 is attached to the base unit by an arm 36. The examiner can use a joystick 37 to move the optical head 2 into alignment with the patient's eye.

The angle of declination and angle of elevation of the optical head 2 can be adjusted relative to the optical axis of the eye by adjusting the arm 36. The image processing unit 5, control panel 59 and TV monitor 4 are also arranged on the table 41.

Under the table 41 is the laser light source unit 6, which can accommodate quite bulky laser light sources. The laser light source unit 6 and optical system unit 2 are connected by an optical fiber 65 which passes through a hole 42 in the table. As has been described, the optical fiber 65 and laser light source unit 6 may be omitted from some system configurations.

Figure 3:
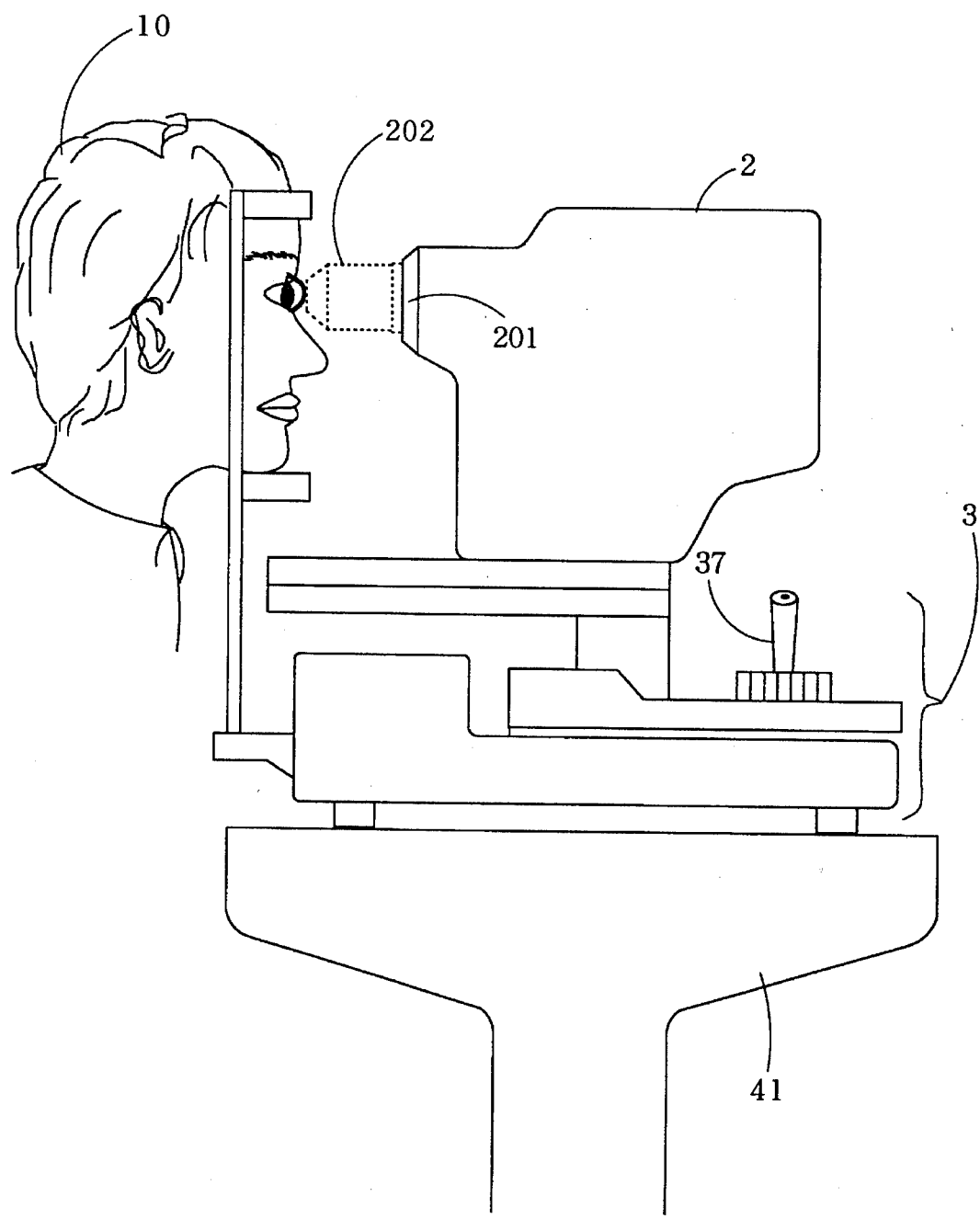
FIG. 3 is a diagram illustrating how images of the anterior chamber of the eye are obtained with the ophthalmic examination apparatus of the invention.

FIG. 3 illustrates an auxiliary optical system unit according to the invention. While the ophthalmic examination apparatus of this invention is usually used to obtain images of the eye fundus, attaching the auxiliary optical system unit 202 (shown in the drawing by the dotted line) to the laser beam emission aperture 201 of the optical system unit 2 enables the anterior chamber of the eye to be observed on a TV monitor.

Figure 4:
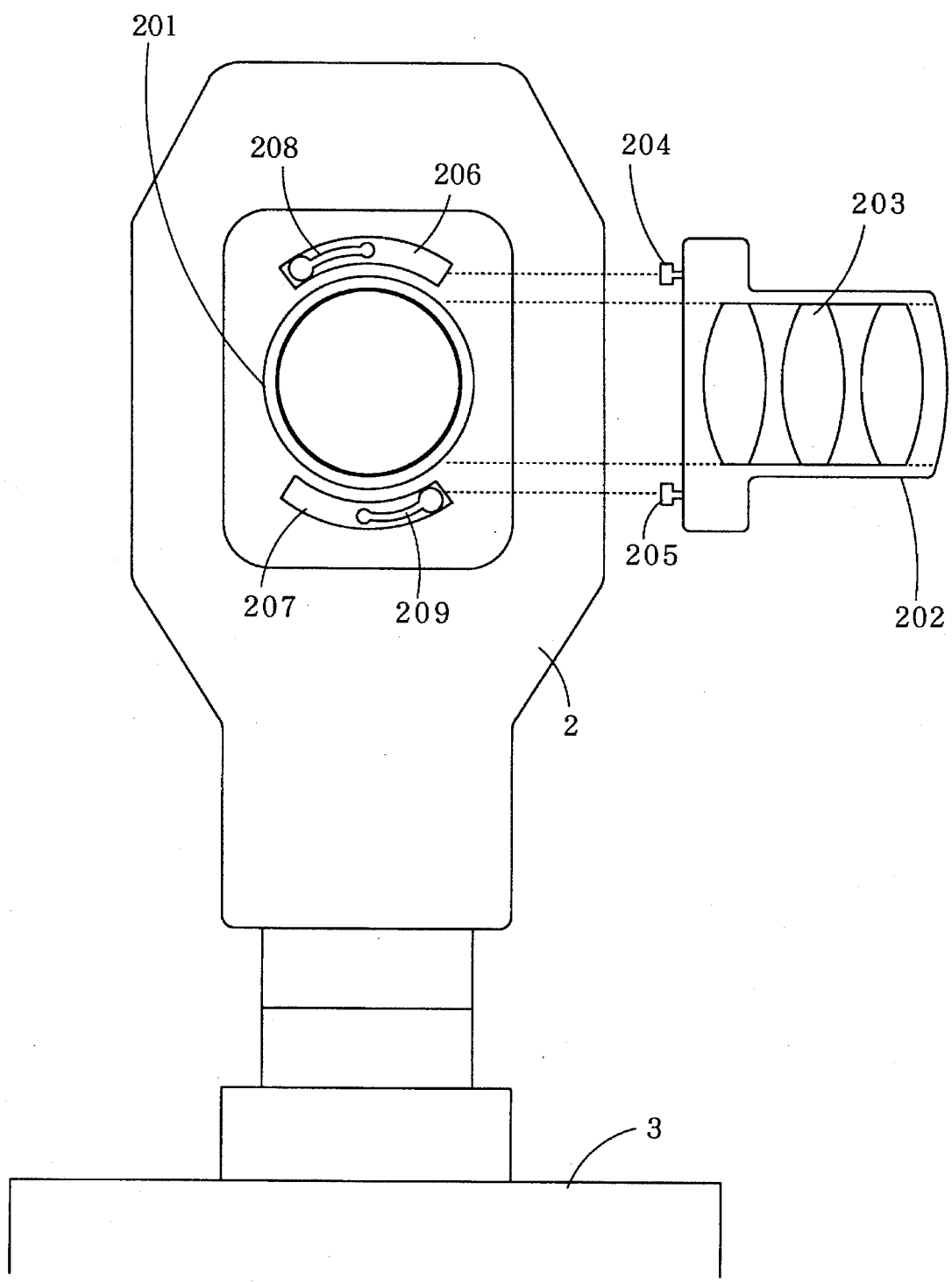
FIG. 4 shows how the auxiliary optical system unit is connected with the main optical system unit.

FIG. 4 shows the mechanism which enables the auxiliary optical system unit 202 to be readily attached to, and detached from, the optical system unit 2. In FIG. 4 the optical system unit 2 is shown from the front at which the patient's eye is directed, while the auxiliary optical system unit 202 is shown at right-angles to the optical axis.

The auxiliary optical system unit 202 has a lens barrel 203 constituted by a plurality of lenses for changing the focal length of the main optical system, and the base of the unit is provided with mounting pins 204 and 205.

A pair of mounting plates 206 and 207 with fixing holes 208 and 209 are provided at the laser beam emission aperture 201. Thus, the auxiliary optical system unit 202 can be securely affixed to the optical system unit 2 by inserting the pins 204 and 205 into the holes 208 and 209 and rotating the unit 202 a prescribed distance clockwise.

The auxiliary optical system unit 202 can be easily removed by pressing it against the optical system unit 2 and turning it counterclockwise. Corneal endothelial cells and other parts of the eye can also be observed microscopically by using a contact type objective lens as the auxiliary optical system unit 202.

Figure 5:
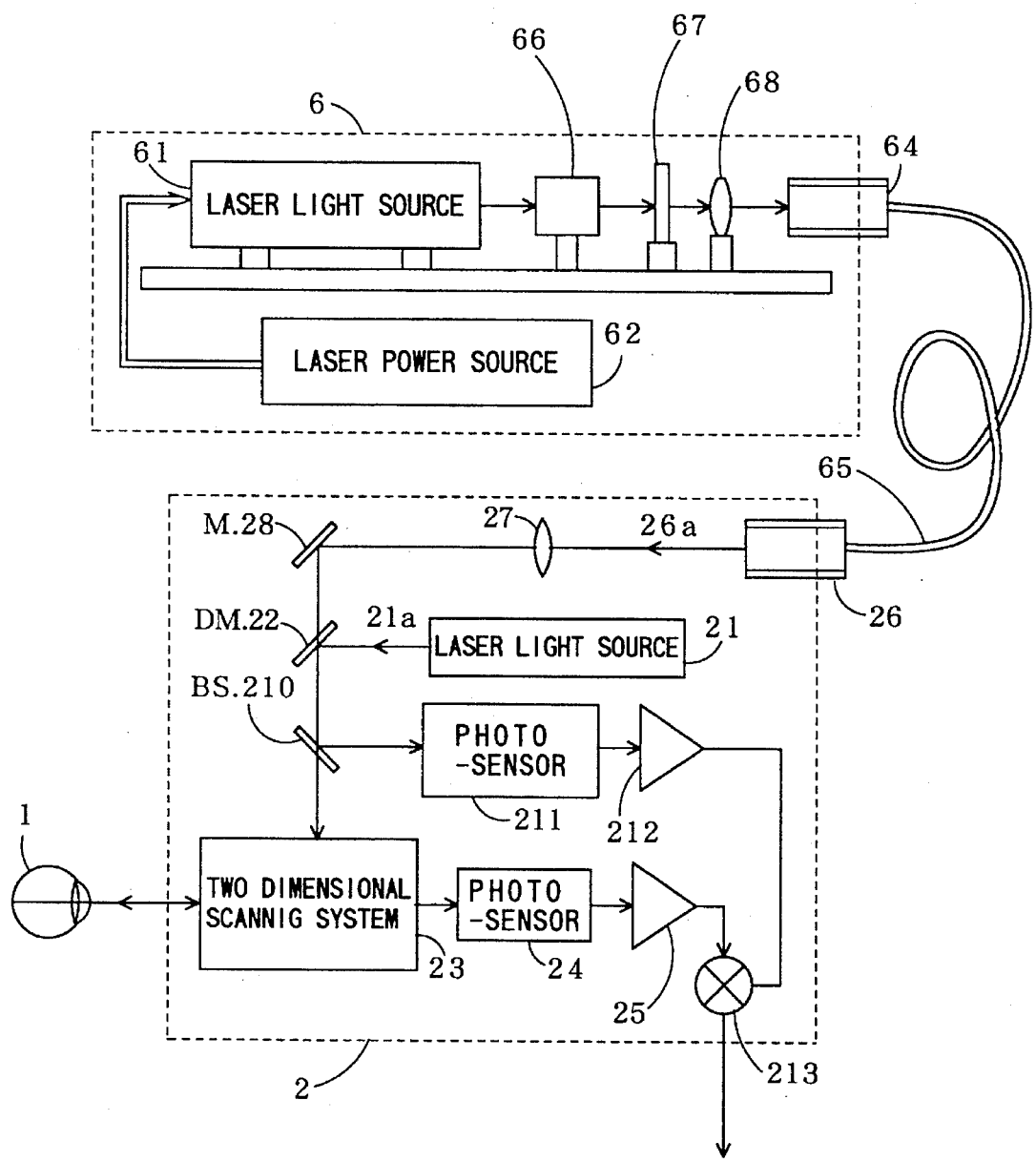
FIG. 5 illustrates the arrangement used to eliminate the effect of laser power variations.

FIG. 5 illustrates a mechanism for suppressing the effects of laser beam power variation, for use in an ophthalmic examination apparatus when it is necessary to obtain precise images with a high S/N ratio. In the laser light source unit 6, the laser beam from the laser light source 61 passes through an optical device 66 such as an optical isolator that controls the direction of optical propagation, a filter 67 and an imaging lens 68, and impinges on the end face of the optical fiber 65 connected by the connector 64. The optical fiber 65 may be single-mode fiber.

The optical isolator 66 is for controlling the direction of light propagation and may be constituted by a Faraday element or a polarizer plate and a ¼-wavelength plate, for example. Incorporating the isolator prevents reverse propagation of light from the end of the optical fiber 65 or elsewhere back into the laser light source 61, which would alestabilize the lasing action. The filter 67 is to enable one wavelength to be selected, such as, for example, in cases where the laser light source 61 is one that is used to emit multiple wavelengths simultaneously. A plurality of filters 67 may be prepared corresponding to the wavelengths of the lasers concerned and arranged so as to be changed electrically, such as by means of a solenoid device and motor (not shown), for example.

A mechanism for compensating for power variations in the laser beam projected by the optical fiber 65 may be incorporated in the optical system unit 2.

With reference to FIG. 5, the laser beam 26a from the optical fiber 65 is combined with the laser beam 21a by the dichroic mirror 22. The composite beam is divided by a beam-splitter 210, with one beam being directed to a monitor photosensor 211. The intensity signal of the laser beam photoelectrically converted by the photosensor 211 is amplified by an amplifier 212 and supplied to a divider 213. The divider 213 is for removing laser beam power variation components superposed on the image signal by dividing the image signal from the prescribed region of the eye fundus obtained from the photosensor 24 by the laser beam intensity monitor signal.

The beam-splitter 210 and the monitor photosensor 211 may be provided in the scanning system 23 to detect part of the scanning laser beam. The arrangement shown in FIG. 5 permits the S/N ratio of the TV picture to be improved, because the video signal showing the region of the eye fundus being examined is not affected by any variation that might occur in the power of the scanning laser beam.

The modular unit construction of the above embodiment in which the system configuration consists of an optical system unit, base unit, image processing unit and laser light source unit enable the size and cost of each of the system modules to be decreased.

Also, the use of an auxiliary optical system unit which can be detachably attached to the main optical system is of major significance, as it makes it possible for the one system to be used to also observe other regions of the eye, such as the anterior chamber, in addition to the fundus, thereby enabling a large amount of diagnostic information to be obtained.

The modular system construction also makes it easy to meet a diverse range of user needs, simplifies maintenance and transport and makes it possible to configure a system very economically.

Moreover, even when an optical fiber is used as the laser beam link, the incorporation of an optical device to control the direction of light propagation and of signal processing means to compensate for laser beam power variations ensures that the effect of such variations does not appear in the video signal output, resulting in high-quality TV monitor images with a high S/N ratio.

As shown in the foregoing, the apparatus according to this invention is comprised of an optical system unit, a base unit, an image processing unit and a laser light source unit, and for an optional auxiliary optical system unit for observing the anterior chamber that can be attached to the main optical system unit. Also, when the units are connected by optical fiber, a further configuration can be used to suppress the effect of beam power variation noise produced by light returning from a fiber end face or other cause.

The modular unit, construction with optional detachably attachable units according to the present invention enable each of the system units to be simplified and the size and cost to be decreased. It also simplifies assembly, adjustment, maintenance and transport. Furthermore the ability to meet diverse ophthalmic requirements quickly by swapping and adding components makes it an extremely economical ophthalmic examination apparatus. Moreover, there is no degradation in image quality even when the laser light source and optical system are linked by optical fibers.

What is claimed is:

1. An ophthalmic examination apparatus in which a laser light beam from a laser light source is projected onto the fundus of an eye and scanned two-dimensionally, and light reflected from the eye fundus is detected by a light receiving element and photoelectrically converted to thereby obtain image information of a prescribed part of the eye fundus, the. ophthalmic examination apparatus comprising:

an optical system having a first laser light source unit for generating a laser light beam of one or more wavelengths, scanning means for scanning the laser light beam two-dimensionally onto the fundus of an eye, and a light receiving element for receiving light reflected from a prescribed part of the eye fundus and converting the intensity of the reflected light into image signals;

a base unit having control means for controlling the scanning means to scan the eye fundus at a prescribed frequency and controlling displacement of the optical system vertically, laterally and at an inclination with respect to the eye;

a second laser light source unit detachably connectable to the optical system for generating a laser light beam of a wavelength different from the wavelength of the laser light beam generated by the first laser light source unit;

an optical fiber detachably connectable between the second laser light source unit and the optical system for transmitting a laser light beam from the second laser light source unit to the optical system;

monitoring means for detecting and monitoring the intensity of the laser light beam transmitted by the optical fiber and outputting a signal representative of the detected intensity;

signal processing means for controlling the intensity of the image outputted by the light receiving element in response to the signal outputted monitoring means; and image processing means for digitally processing and storing the image signals outputted by the light receiving element.

2. An ophthalmic examination apparatus according to claim 1; wherein the monitoring means and the signal processing means are included in the optical system, 3. An ophthalmic examination apparatus according to claim 1; wherein the signal processing means comprises an amplifier circuit for amplifying the signal outputted by the monitoring means, and circuit means for eliminating intensity.

4. An ophthalmic examination apparatus according to claim 1; further comprising support means for supporting the optical system, the base unit and the imaging processing means as an integral unit, 5. An ophthalmic examination apparatus according to claim 1; wherein the optical fiber is a single-mode optical fiber, 6. An ophthalmic examination apparatus according to claim 1; further comprising an external auxiliary optical system unit for observing the anterior chamber of the eye, 7. An ophthalmic examination apparatus according to claim 6; wherein the optical system comprises an aperture member for emission of a laser light beam, and a mounting plate connected to the aperture member for attaching the auxiliary optical system to the aperture member, 8. An ophthalmic examination apparatus according to claim 1; further comprising an optical element disposed in the light path between the second laser light source and the optical fiber for regulating the direction of propagation of the laser light beam generated by the second laser light source.

9. An ophthalmic examination apparatus according to claim 8; wherein the optical element comprises a wavelenght plate.

10. An ophthalmic examination apparatus according to claim 8; wherein the optical element comprises a Faraday element.

11. An ophthalmic examination apparatus in which a laser light beam from a laser light source is projected onto the fundus of an eye and scanned two-dimensionally, and light reflected by the eye fundus is detected by a light receiving element and photoelectrically converted to thereby obtain image information of a prescribed part of the eye fundus, the ophthalmic examination apparatus comprising:

a laser light source unit for generating a laser light beam of one or more wavelengths;

an optical fiber for transmitting the laser light beam;

means for projecting the laser light beam transmitted by the optical fiber onto the fundus of an eye;

a light receiving element for receiving light reflected from a prescribed part of the eye fundus and converting the intensity of the reflected light into image signals;

monitoring means for detecting and monitoring the intensity of the laser light beam transmitted by the optical fiber and outputting a signal representative of the detected intensity; and signal processing means for controlling the intensity of the image signals outputted by the light receiving element in response to the signal outputted by the monitoring means to eliminate influence of intensity fluctuations of the laser light beam from the image signals.

12. An ophthalmic examination apparatus according to claim 11, wherein the signal processing means comprises an amplifier circuit for amplifying the signal outputted by the monitoring means, and a divider circuit for eliminating the intensity fluctuations.

13. An ophthalmic examination apparatus according to claim 11; further comprising an optical element disposed in the light path between the second laser light source and the optical fiber for regulating the direction of propagation of the laser light beam generated by the second laser light source.

14. An ophthalmic examination apparatus according to claim 13; wherein the optical element comprises a wavelength plate.

15. An ophthalmic examination apparatus according to claim 13; wherein the optical element comprises a Faraday element.

16. An ophthalmic examination apparatus comprising: an optical system having first light source means for generating a light beam, scanning means for scanning the light beam two-dimensionally onto a predetermined portion of an eve, and light receiving means for receiving light reflected from the predetermined eye portion and converting the intensity of the reflected light into image signals; a base unit having control means for controlling the scanning means to scan the predetermined eye portion at a prescribed frequency and controlling displacement of the optical system vertically, laterally and at an inclination with respect to the eye, and image processing means for processing the image signals outputted by the light receiving element; second light source means detachably connectable to the optical system for generating a laser light beam of a wavelength different from the wavelength of the light beam generated by the first light source means; an optical fiber detachably connecting the second light source means with the optical system for transmitting a light beam from the second light source means to the optical system; monitoring means for detecting and monitoring the intensity of the light beam transmitted by the optical fiber and outputting a signal representative of the detected intensity; and signal processing means for controlling the intensity of the image signals outputted by the light receiving means in response to the signal outputted by the monitoring means.

17. An ophthalmic examination apparatus according to claim 16; wherein the signal processing means comprises in amplifier circuit for amplifying the signal outputted by the monitoring means, and a divider circuit for eliminating intensity fluctuations of the signal outputted by the monitoring means from the image signals outputted by the light receiving means.

* * * * *